US008084068B2

(12) United States Patent
Noordam et al.

(10) Patent No.: US 8,084,068 B2
(45) Date of Patent: *Dec. 27, 2011

(54) PROCESS FOR THE PRODUCTION OF COMPOSITIONS CONTAINING RIBONUCLEOTIDES AND THEIR USE AS FLAVOURING AGENTS

(75) Inventors: Bertus Noordam, 's-Gravenzande (NL); Jan Gerrit Kortes, Leusden (NL)

(73) Assignee: DSM IP Assets B.V., Heerlen (NL)

( * ) Notice: Subject to any disclaimer, the term of this patent is extended or adjusted under 35 U.S.C. 154(b) by 1381 days.

This patent is subject to a terminal disclaimer.

(21) Appl. No.: 10/584,847

(22) PCT Filed: Jan. 6, 2005

(86) PCT No.: PCT/EP2005/000120
§ 371 (c)(1),
(2), (4) Date: Jun. 28, 2006

(87) PCT Pub. No.: WO2005/067734
PCT Pub. Date: Jul. 28, 2005

(65) Prior Publication Data
US 2009/0148559 A1    Jun. 11, 2009

(30) Foreign Application Priority Data

Jan. 9, 2004   (EP) .................................. 04075072

(51) Int. Cl.
*A23L 1/28* (2006.01)
(52) U.S. Cl. ............ 426/60; 426/537; 536/127; 435/89; 435/270
(58) Field of Classification Search .................. None
See application file for complete search history.

(56) References Cited

U.S. PATENT DOCUMENTS 4,303,680 A   12/1981   Tanekawa et al.
4,851,390 A *  7/1989   Morishige ................... 514/44 R

FOREIGN PATENT DOCUMENTS

| EP | 0 299 078 | 1/1989 |
| EP | 0 354 610 | 2/1990 |
| EP | 1 080 645 | 3/2001 |
| WO | WO 03/063613 A1 | 8/2003 |
| WO | WO 03/063614 A1 | 8/2003 |

OTHER PUBLICATIONS

Halasz, Anna and Radomir Lasztity. Use of Yeast Biomass in Food Production, 1991, CRC Press, Inc: pp. 115-122 and p. 248.*
Written Opinion issued in connection with PCT/EP20005/000120.
Sommer R, "Hefeautolysate—Herstellung, Eigenschafen und Anwendung bei Fertiggerichten", Lebensmittelechnik, vol. 16, No. 1/2, 1984, pp. 30-31.
Anon: "Formulating lower-fat and lower-salt . . . Processed Meats. Multifunctional flavorings aid in developing 'healthier' processed meats with acceptable taste and texture", Chilton's Food Engineering, vol. 61, No. 9, Sep. 1989, pp. 46, 48.
International Search Report, PCT/EP2005/000120 Jul. 2005 pp. 1 and 2 and 3rd pg.

* cited by examiner

*Primary Examiner* — Humera Sheikh
*Assistant Examiner* — Felicia King
(74) *Attorney, Agent, or Firm* — Baker, Donelson, Bearman, Caldwell & Berkowitz, PC

(57) ABSTRACT

The present invention describes a process to produce a composition containing 5'-ribonucleotides wherein a microorganism is subjected to autolysis under conditions at which a substantial part of the RNA remains in a form degradable into 5'-ribonucleotides and at which a substantial part of the RNA remains associated with the cell wall fraction. Said cell wall fraction is recovered by a solid/liquid separation method and the RNA associated with said wall fraction is converted into 5'-ribonucleotides. The present invention also describes compositions containing 5'-ribonucleotides and their use in food or feed.

12 Claims, No Drawings

PROCESS FOR THE PRODUCTION OF COMPOSITIONS CONTAINING RIBONUCLEOTIDES AND THEIR USE AS FLAVOURING AGENTS

This application is the U.S. national phase of international application PCT/EP2005/000120 filed 6 Jan. 2005 which designated the U.S. and claims benefit of EP 04075072.1, dated 9 Jan. 2004, the entire content of which is hereby incorporated by reference.

FIELD OF THE INVENTION

The present invention relates to a process to produce a composition containing 5'-ribonucleotides. The invention further relates to a compositions containing 5'-ribonucleotides and to the use of said compositions in food or feed.

BACKGROUND OF THE INVENTION

Autolytic yeast extracts are concentrates of the soluble materials obtained from yeast after disruption of the cells and digestion (lysis) of the polymeric yeast material. The active yeast enzymes released in the medium after cell disruption contribute to the lysis. These types of yeast extract are rich in amino acids and generally do not comprise 5'-ribonucleotides because during the autolytic process the native RNA is decomposed or modified in a form which is not degradable into 5'-ribonucleotides. They are used in the food industry as basic taste providers. The amino acids present in the yeast extract add a bouillon-type brothy taste to the food.

Hydrolytic yeast extracts, on the other hand, are concentrates of the soluble materials obtained from yeast after disruption of the cells, digestion (lysis) and addition of proteases and/or peptidases and especially nucleases to the yeast suspension during lysis. The native yeast enzymes are inactivated prior to the lysis. During this process, 5'-ribonucleotides of guanine (5'-guanine mono phosphate; 5'-GMP), uracil (5'-uracil mono phosphate; 5'-UMP), cytosine (5'-cytosine mono phosphate; 5'-CMP) and adenine (5'-adenine mono phosphate; 5'-AMP) are formed. When adenylic deaminase is added to the mixture, 5'-AMP is transformed into 5'-inosine mono phosphate (5'-IMP). The hydrolytic yeast extracts obtained by this method are therefore rich in 5'-ribonucleotides, especially rich in 5'-GMP and 5'-IMP. Often yeast extracts are also rich in mono sodium glutamate (MSG). 5'-IMP, 5'-GMP and MSG are known for their flavour enhancing properties. They are capable of enhancing the savoury and delicious taste in certain types of food. This phenomenon is described as 'mouthfeel' or umami.

Yeast extracts rich in 5'-ribonucleotides and, optionally, rich in MSG, are usually added to soups, sauces, marinades and flavour seasonings.

Yeast extracts rich in 5'-ribonucleotides are up to date produced using yeast strains with high RNA content and/or by partial extraction of the cell content.

A disadvantage of this type of taste enhancing hydrolytic yeast extracts is that, due to the presence of amino acids and short peptides and of others yeast components, they are not very suitable for applications which require cleanliness of taste.

U.S. Pat. No. 4,303,680 describes the production of a yeast extract containing 5'-ribonucleotides using an autolytic process under conditions at which the intracellular RNA is only partially decomposed and remains bound to the autolysed cells. The protein content of the cells is hydrolysed in oligopeptides and amino acids. The RNA is enzymatically transformed into 5'-ribonucleotides only after the RNA has been released in solution from the autolysed cells by means of a heat treatment. With this method a yeast extract is obtained which is rich in amino acids, oligopeptides and other components like carbohydrates, minerals, lipids and vitamins. The presence of these components imparts to this yeast extract a bouillon-like, brothy taste which is not desirable in some food applications. A further disadvantage is that the yeast extract comprises a relatively low amount of 5'-ribonucleotides.

An object of the present invention is to provide a process for the production of a composition containing 5'-ribonucleotides which is based on autolysis of a microorganism wherein the composition obtained comprises at least 15% w/w of 5'-ribonucleotides and wherein said composition is clean in taste. The process is very simple and cost-effective and therefore commercially very attractive. Another object of the present invention is to provide compositions containing 5'-ribonucleotides with the above-mentioned characteristics and comprising an amount of 5'-ribonucleotides, based on sodium chloride free dry matter of the composition, of at least 15% w/w and less than 55% w/w. A further object of the present invention is to provide the use of the compositions of the inventions in food, beverages and feed.

DETAILED DESCRIPTION OF THE INVENTION

In a first aspect the present invention provides a process to produce a composition containing 5'-ribonucleotides comprising:
  a) subjecting a microorganism to autolysis under conditions at which a substantial part of the RNA remains in a form degradable into 5'-ribonucleotides and at which a substantial part of the RNA remains associated with the cell wall fraction;
  b) subjecting the autolysate to solid/liquid separation and recovering the RNA-containing cell wall fraction;
  c) converting the RNA in the recovered RNA-containing cell wall fraction into 5'-ribonucleotides.

With the term "5'-ribonucleotides" it is herewith intended a mixture of 5'-GMP, 5'-CMP, 5'-UMP and further 5'-AMP and/or 5'-IMP, wherein said 5'-AMP may be either partially or completely converted into 5'-IMP.

The term "5'-ribonucleotide(s)" encompasses the free 5'-ribonucleotide as well as a salt thereof.

In the context of the present invention autolysis of a microorganism is defined as a process wherein degradation of the microbial cells and of the polymeric microbial material is at least partially effected by active native microbial enzymes released in the medium after (partially) damaging and/or disrupting the microbial cell wall.

Any microorganism can be used as natural source of RNA in the process of the invention. Bacterial and fungal microorganisms are preferred, such as those which are suitable for food and feed applications. Preferred microorganisms are those that have the status of being food-grade and that can be safely applied in food for human consumption. Bacterial or fungal strains with a high RNA content (i.e. with an RNA content of typically 6-15%) enable the production of compositions with a high amount of 5'-ribonucleotides. However an advantage of the process of the invention is that also bacterial or fungal strains with a relatively low RNA content can be used. These strains can be advantageously used for the preparation of compositions containing a higher 5'-ribonucleotide content than would be expected on basis of the RNA content of the starting strain.

Examples of preferred microorganisms include filamentous fungi such as *Trichoderma* or *Aspergillus*, and yeasts such as *Saccharomyces, Kluyveromyces* and *Candida*. Strains belonging to the genus *Saccharomyces*, in particular belonging to the species *Saccharomyces cerevisiae* are most preferred.

Examples of suitable bacterial microorganisms are lactic acid bacteria, e.g. *Lactobacillus*.

The microorganism used in the process of the invention may be prepared by any suitable fermentation process known in the art. The microbial biomass may be concentrated prior to its use in the present process, for example by centrifugation or filtration. For example, cream yeast (baker's yeast which has been concentrated to 15-27% w/w) may be used. Optionally fermentation broths comprising Brewer's yeast or residue yeast derived from breweries (spent Brewer's yeast) may be used.

The present invention provides a process which is especially suitable for large scale production of compositions containing 5'-ribonucleotides. Large scale means that fermentation is performed in fermentors of more than 10 $m^3$.

The autolytic process is initiated by damaging and/or partially disrupting the microbial cell walls. This way the cells are partially opened and at least some of the cell content is released. In order to damage and/or partially disrupt the microbial cell walls, the cells are treated chemically, mechanically or enzymatically using methods known to those skilled in the art.

Mechanical treatments include homogenisation techniques. At this purpose, use of high-pressure homogenisers is possible. Other homogenisation techniques may include mixing with particles, e.g. sand and/or glass beads, or the use of a milling apparatus (e.g. a bead mill).

Chemical treatments include the use of salts, alkali and/or one or more surfactants or detergents. Chemical treatments are less preferred because they may lead to partial degradation of RNA especially when alkali is used, with consequent formation of 2'-ribonucleotides and 3'-ribonucleotides.

Preferably damaging and/or partially disrupting the microbial cell wall is done enzymatically because a better control of the process can thereby be achieved and because this method is especially suitable to be used at large scale. Several enzyme preparations can be used like cellulases, glucanases, hemicellulases, chitinases, proteases and/or pectinases. Preferably protease is used, more preferably endoprotease is used. The conditions used to initiate the autolytic process are dependent on the type of enzyme used and can be easily determined by those skilled in the art. Generally the conditions used to enzymatically damage and/or disrupt the microbial cell wall will correspond to those applied during the autolysis of the microorganism.

The autolysis of the microorganism is at least partially effected by active native microbial enzymes released in solution after (partially) damaging and/or disrupting the microbial cell wall wherein the chemicals, or more preferably, the enzymes added to damage and/or to disrupt the microbial cell wall may contribute to the degradation of the microbial cells and of polymeric microbial material.

In the process of the invention the conditions used in the autolytic process are such that a substantial part of the RNA remains in a form degradable into 5'-ribonucleotides. In this context, with "substantial part of the RNA" is meant preferably at least 50%, more preferably at least 60%, most preferably at least 70%. Thus, the RNA does not need to remain fully intact during the autolytic process, but at least a substantial part of the RNA should remain in a form degradable into 5'-ribonucleotides. Generally up to 100% of the RNA may remain in a form degradable into 5'-ribonucleotides. In a form degradable into 5'-ribonucleotides means that the RNA should be in a form that allows conversion into 5'-ribonucleotides by a suitable enzyme. Preferably the suitable enzyme is a 5'-phosphodiesterase (5'-Fdase).

A form of RNA degradable into 5'-ribonucleotides comprises oligonucleotides containing at least two ribonucleotide units. Therefore RNA in a form degradable into 5'-ribonucleotides may consist of a mixture comprising intact RNA and oligonucleotides or polynucleotides of different lengths. In the context of the present invention an oligonucleotide comprises 2-10 ribonucleotide units, while a polynucleotide comprises more than 10 ribonucleotide units.

In the process of the invention the conditions used in the autolytic process are such that during the autolysis a substantial part of the RNA remains associated with the cell wall fraction, i.e. remains inside the damaged cells and/or bound to the cell walls or fragments thereof. In this context, with "substantial part of the RNA" is meant preferably at least 20%, more preferably at least 30%, most preferably at least 40%. Generally up to 90% of the RNA may remain associated with the cell wall fraction.

The percentage of RNA, which remains in a form degradable into 5'-ribonucleotides during the autolytic process is defined as the ratio (×100) between a) the weight percentage of 5'-GMP (calculated as the disodium heptahydrate thereof and based on sodium chloride free dry matter) measured in the autolysate after inactivation of the enzymes participating in the autolysis and conversion of RNA into 5'-ribonucleotides, and b) the weight percentage of GMP (calculated as the disodium heptahydrate thereof and based on sodium chloride free dry matter) measured in the starting material after complete alkaline hydrolysis of RNA. The weight percentage of GMP (calculated as the disodium heptahydrate thereof and based on sodium chloride free dry matter) measured in the starting material after alkaline hydrolysis can be determined from the corresponding weight percentage of free GMP (based on sodium chloride free dry matter) by multiplying the latter with a factor 1.47. The method to determine the amount of 5'-GMP in the autolysate and of GMP after basic hydrolysis is described in example 1. The method used to determine the amount of 5'-GMP can also be used to determine the amount of 5'-IMP, 5'-AMP, 5'-CMP and 5'-UMP if necessary with some modifications well within the knowledge of those skilled in the art.

The percentage of the RNA, which remains associated with the cell wall fraction is defined as the ratio (×100) between a) the amount of RNA in grams in the cell wall fraction of an autolysate originating from a fixed amount of starting material, and b) the amount of RNA in grams present in the same fixed amount of starting material. The method to determine the amount of RNA in the cell wall fraction and in the starting material is described in example 1.

The conditions applied in the autolysis to ensure that a substantial part of the RNA remains in a form degradable into 5-ribonucleotides and that a substantial part of the RNA remains associated with the cell wall fraction, will be generally dependent on the microorganism used. These conditions can be easily determined by those skilled in the art by varying process parameters like temperature and/or pH and/or the time period at which a particular temperature and/or pH is maintained during autolysis and subsequently determining the effect of such process parameter(s) on the amount of RNA which remains in a form degradable into 5-ribonucleotides and/or which remains associated with the cell wall fraction.

In particular the first phase of autolysis is performed at a particular pH range combined with a particular temperature. For instance, the conditions applied in the autolysis of *Saccharomyces cerevisiae* to ensure that a substantial part of the RNA remains in a form degradable into 5'-ribonucleotides and that a substantial part of the RNA remains associated with the cell wall fraction are such that the pH in the first phase of the autolysis is between 4.5-9 and/or the temperature is between 50-65° C. Preferably the first 8 hours of the autolysis, more preferably the first 4 hours of the autolysis, are performed at a pH of 4.5-5.5 and at a temperature of 57-65° C., or at a pH 5.5-9 and a temperature of 50-65° C.

The conditions to be kept after the first phase of the autolysis are less critical. After the first phase the pH is generally kept between 4 and 10 and the temperature is generally kept between 40° C. and 70° C. In general the duration of the autolytic process including the first phase is at most 24 hours.

The present invention may encompass as well a process wherein in step a) a microorganism is subjected to hydrolysis under conditions at which a substantial part of the RNA remains in a form degradable into 5'-ribonucleotides and at which a substantial part of the RNA remains associated with the cell wall fraction. In the context of the present invention hydrolysis of a microorganism is defined as a process wherein the native microbial enzymes have been inactivated and wherein suitable exogenous enzymes added to the microbial biomass to effect degradation of the microbial cells and of the polymeric microbial material.

After autolysis a suspension (autolysate) is obtained which comprises a microbial cell wall fraction, RNA which is for a substantial part in a form degradable into 5'-ribonucleotides and which is for a substantial part associated with the cell wall fraction, and soluble cell components (e.g. proteins, carbohydrates, etcetera). The cell wall fraction comprises insoluble cell residues, in particular cell walls or fragments thereof.

At the end of the autolytic process and prior to step b), the chemicals used for damaging and/or partially disrupting the microbial cell walls and/or the enzymes which took part in the autolytic process should preferably be neutralised and/or inactivated. The enzymes which took part in the autolysis, are the native microbial enzymes and optionally any added exogenous enzyme used to initiate the autolytic process. Neutralisation and/or inactivation of the chemicals and/or the enzymes should occur under conditions at which a substantial part of the RNA remains in a form degradable into 5'-ribonucleotides and wherein a substantial part of the RNA remains associated with the cell wall fraction. Inactivation of the enzymes which took part in the autolysis can be done by pH treatment or preferably by a heat treatment whereby the enzymes are inactivated, a substantial part of the RNA remains in a form degradable into 5'-ribonucleotides and wherein a substantial part of the RNA remains associated with the cell wall fraction. The enzymes can be inactivated by heat treatment, for instance by heating the mixture from 5 minutes to 1 hour at a temperature from 65° C. to 95° C., more preferably by heating from 30 minutes to 1 hour at a temperature from 65° C. to 75° C., wherein typically a shorter reaction time may be used at higher reaction temperatures. For example, heating the mixture for 1 hour at 65° C., or for 30 minutes at 75° C. may be sufficient to inactivate the enzymes whereby a substantial part of the RNA remains in a form degradable into 5'-ribonucleotides and wherein a substantial part of the RNA remains associated with the cell wall fraction.

In step b) of the process of the invention the autolysate is subjected to solid/liquid separation and the RNA-containing cell wall fraction is recovered.

The RNA-containing cell wall fraction is preferably recovered by common solid-liquid separation methods, preferably by centrifugation or filtration. Use of centrifugation or filtration is economically advantageous in particular when the process is performed at large scale.

In order to increase the amount of recovered RNA in a form degradable into 5'-ribonucleotides, the autolysate may be subjected to ultra filtration (UF) instead of to a common solid-liquid separation method like centrifugation or filtration. In this way, a mixture of the RNA-containing cell wall fraction and RNA derived from the microbial soluble fraction is recovered. Thus, not only the RNA associated with the cell wall fraction is separated from the microbial soluble fraction but also the RNA which had been released into solution during autolysis. In cases where UF is used to recover RNA, preferably membranes with a molecular weight cut off from 10 to 50 kD or preferably from 20 to 50 kD can be used. In general a larger molecular weight cut off allows a higher flow rate through the membrane, but might result in larger losses and/or less pure products. The type of solid-liquid separation used and the efficiency of said solid-liquid separation can influence, among other factors, the amount of 5'-ribonucleotides obtained in the compositions of the invention.

The RNA in the recovered fraction is converted into 5'-ribonucleotides. This is done by enzymatically treating the RNA-containing cell wall fraction, optionally mixed with RNA derived from the microbial soluble fraction obtained by UF.

5'-phosphodiesterase (5'-Fdase) is preferably used to convert RNA into 5'-ribonucleotides. 5'-phosphodiesterase can be obtained from a microbial or a vegetable source (for example a malt root extract). An example of a commercially available microbial 5'-Fdase is Enzyme RP-1 produced by Amano (Japan).

Optionally, 5'-AMP is converted to 5'-IMP by a deaminase, for example adenyl deaminase. An example of a commercially available deaminase is Deaminase 500 produced by Amano (Japan).

Treatment of RNA by 5'-Fdase and deaminase can be performed in a two-step or in a single step process.

After conversion of the RNA into 5'-ribonucleotides the fraction containing 5'-ribonucleotides preferably is separated from the cell wall fraction. Said separation may be achieved by centrifugation or filtration or by any other method suitable to achieve solid/liquid separation.

In an embodiment, the fraction containing 5'-ribonucleotides is purified from components having a higher molecular weight than the 5'-ribonucleotides by ultrafiltration. The degree of purification will depend on the molecular weight cut-off of the ultrafiltration membrane used. Ultra filtration membranes as mentioned above can e.g. be used.

It will be understood that in the context of the present invention a wording like "recovering the RNA" or "converting the RNA" does not necessarily mean that all RNA is recovered or converted, respectively. It will be clear to those skilled in the art that the amount of the RNA which is recovered will depend on the type of separation method used. It will also be clear that the amount of RNA which is converted will depend on several factors, one of which is the accessibility of the RNA associated with the cell wall insoluble fraction to the enzymes used in this step.

The present invention provides a process which is especially useful for large-scale separation of RNA and which allows the production of compositions containing 5'-ribonucleotides on a commercially attractive and large scale for use in food and feed applications. The present invention provides a process, which results in a good purity of the composition containing 5'-ribonucleotides and rather low losses.

In a second aspect, the present invention provides a composition containing 5'-ribonucleotides, obtainable by the process of the first aspect, comprising an amount of 5'-ribonucleotides, based on sodium chloride free dry matter of the composition, of at least 15% w/w and less than 55% w/w, preferably of at least 30% w/w and less than 55% w/w, more preferably of at least 40% w/w and less than 55% w/w. This composition has a high 5'-ribonucleotide content, is clean in taste and has several applications in food or feed.

The amount of 5'-ribonucleotide such as 5'-GMP, 5'-AMP and 5'-IMP in the composition of the invention is given as weight percentage (% w/w) that is based on sodium chloride free dry matter of the composition. The weight percentage of 5'-ribonucleotide is calculated based on the disodium salt heptahydrate thereof unless otherwise specified. Sodium chloride free does not mean that the composition of the invention cannot contain sodium chloride, but means that for the calculation of the weight percentage the weight of sodium chloride is excluded from the composition. The measurement of sodium chloride in the composition and the above-mentioned calculation can be performed by methods known to those skilled in the art.

Preferably the composition of the invention comprises a higher amount of 5'-GMP than the sum of the amounts of 5'-AMP and 5'-IMP. This is advantageous because 5'-GMP is more functional than 5'-IMP with respect to flavour enhancement, while 5'-AMP does not contribute to flavour enhancement (T. Nagodawithana, Savoury Flavours, (1995) edited by Esteekay associates, Inc, Wisconsin, USA, page 302).

Commercially available yeast extracts comprising 5'-ribonucleotides all contain a lower amount of 5'-GMP than the sum of the amounts of 5'-IMP and 5'-AMP. Therefore the composition of the invention has a stronger flavour enhancement than presently commercially available yeast extracts.

The composition of the invention preferably comprises glutamate, wherein the ratio of glutamate to 5'-ribonucleotides is preferably at most 0.1, more preferably at most 0.05, most preferably at most 0.01. The lower limit of the ratio glutamate/5'-ribonucleotides is typically 0.001. The glutamate content of the composition of the invention may vary from 0.01 to 10% w/w, preferably from 0.05 to 5% w/w, more preferably from 0.1 to 2% w/w of glutamate based on sodium chloride free dry matter of the composition.

The amount of glutamate in the composition is given as weight percentage (% w/w) of free glutamic acid and is based on sodium chloride free dry matter of the composition.

The composition of the second aspect of the invention generally comprises less than 10% w/w sodium chloride based on dry matter of the composition, preferably at most 5% w/w, more preferably at most 2% w/w, even more preferably at most 1% w/w.

The composition containing 5'-ribonucleotides according to the invention, has a high 5'-ribonucleotide content, is clean in taste and has several applications in food or feed. Throughout this specification the wording "clean in taste" means that when the composition of the invention is added to food or feed in proper amounts, any particular taste and/or note typical of the microorganism from which the composition is obtained, or any brothy, bouillon-like taste and/or note coming from the composition is minimal or absent in said food or feed. Preferably any particular taste and/or smell and/or note typical of the microorganism is minimal or absent in the composition of the invention. For example, the composition may not have a "yeast" taste or smell in cases where *Saccharomyces* was used as the starting material or may not have a sweet taste in cases where *Candida* was used as the starting material.

The composition containing 5'-ribonucleotides according to the invention can be used in any food or feed product. In the context of the present invention the word "food" means either a nutriment in solid form or a beverage.

According to an embodiment of the invention the composition containing 5'-ribonucleotides according to the invention can be added to any conventional yeast extract in any desired amount. This allows the preparation of a yeast extract having any desired 5'-ribonucleotide content. The compositions of the invention originate from natural sources, i.e. microorganisms which are preferably food grade: The latter makes them very suitable for addition to food or feed.

The composition of the second aspect of the invention can be used to improve and/or enhance the taste and/or aroma of several types of food. Typical types of food to which said composition can be added include dairy food, bakery food, vegetables, fruit, meat, confectionery, beverages or any processed food derived thereof.

The composition of the second aspect of the invention finds a suitable application in food with reduced fat or with low fat. In the context of the present invention, the food with a reduced fat or with low fat is generally obtained from a corresponding full fat food by any processing, alteration, formulation or reformulation which leads to the lowering of the fat comprised therein and/or replacement of said fat with a fat replacer. Said processes and said fat replacers are known in the art. Fat in the context of the present invention means "total fat", i.e. fat containing both saturated and unsaturated fatty acids. The terms "reduced fat" and "low fat" are food labels commonly used in nutrition language. They are also defined by the Food Drug Administration in the US Code of Federal Regulation, Title 21, Vol. 2, Part 101 "Food labelling", Sec. 101.62(b) (revised as of Apr. 1, 2002) (abbreviated as 21 CFR 101.62(b)).

A clear disadvantage of food with reduced fat or with low fat is that this type of food lacks the richness of flavour of the corresponding full-fat food. This disadvantage can be overcome by using the composition of the second aspect of the invention to improve the fat note in the taste and/or in the aroma and/or in the mouthfeel of food with reduced fat or low fat. The latter means that said food with a reduced fat or low fat comprising the composition has taste and/or aroma and/or mouthfeel that has more resemblance with the taste and/or aroma and/or mouthfeel of the corresponding full-fat food as compared with the reduced fat food or low fat food as such.

The composition of the second aspect of the invention finds another suitable application in food comprising artificial sweeteners. A clear disadvantage related to the use of artificial sweeteners is the presence or development of side or after taste, for example bitterness in the artificially flavoured foodstuff. The most common artificial sweeteners, which present the above-mentioned problems when used alone or in combination, are: acesulfame-K, alitame, aspartame, cyclamate, neotame, neohesperidine, saccharin, stevioside, sucralose, and thaumatin. This disadvantage can be overcome by using the composition of the second aspect of the invention to mask the side or after taste of an artificial sweetener in food. The present invention also encompasses a composition comprising an artificial sweetener and the composition of the second aspect.

The composition of the second aspect of the invention can be used to improve the taste and/or aroma and/or mouthfeel of beverages in more specific terms, in particular to improve the specific vegetable note and/or fruity note and/or alcoholic note in the taste and/or aroma of a beverage. For example they can be used to improve the specific vegetable taste and/or vegetable aroma of vegetable juice, the specific fruit taste and/or fruit aroma of fruit juice or the specific alcoholic taste and/or alcoholic aroma of alcoholic beverage like wine and beer, especially those alcoholic beverages with a low or reduced alcoholic content.

The amount of 5'-ribonucleotide composition to be added to the food in the above-mentioned applications will depend on the type of food and on the application. The amount of 5'-ribonucleotide composition can vary for example between 0.0001% w/w and 10% w/w in respect of the food or beverage.

The invention will now be illustrated by some examples which however do not intend to be limiting.

EXAMPLE 1

Preparation of a Composition Comprising 5'-Ribonucleotides Using an Autolytic Process 2 l of cream yeast from *Saccharomyces cerevisiae* was warmed up to 60° C. Subsequently 0.4 ml Pescalase (commercially available serine protease from DSM N.V., The Netherlands) was added and the mixture was incubated for 4 hours at pH 6.0 and 60° C. The conditions were adjusted to pH 5.1 and 51.5° C. and an additional 2 ml of Pescalase was added to the reaction mixture. The mixture was incubated for 20 hours at pH 5.1, 51.5° C. Next, the mixture or autolysate was heated for 1 hour at 65° C. to inactivate all enzyme activity. The extract (soluble fraction) was separated from the insoluble cell walls by means of centrifugation.

The resulting cell wall fraction was treated with 5'-phosphodiesterase to hydrolyse the RNA into 5'-ribonucleotides at a temperature of 65° C. and a pH of 5.3. Next the 5'-AMP was converted by the enzyme deaminase into 5'-IMP at a temperature of 55° C. and at pH 5.1. Finally, the 5'-ribonucleotides were separated from the insoluble cell wall fraction by means of centrifugation.

Samples of the starting cream yeast, of the autolysate, of the supernatant after the first centrifugation, of the cell walls fraction and of the supernatant after the second centrifugation, i.e. after 5'-Fdase and deaminase treatment, were analysed on RNA content and/or on 5'-ribonucleotides content by means of HPLC according to the following methods. RNA in the samples was hydrolysed during an alkaline treatment. GMP (i.e. 2'-GMP and 3'-GMP derived from the hydrolysis of RNA) was quantified by means of HPLC, using 5'-GMP as a standard, using a Whatman Partisil 10-SAX column, a phosphate buffer at pH 3.35 as eluent and UV detection. The weight percentage of RNA content based on sodium chloride free dry matter corresponds to ~4 times the weight percentage of free GMP based on sodium chloride free dry matter.

Some samples were also incubated with 5'-Fdase in order to establish whether the RNA present in the samples could be converted into 5'-ribonucleotides (i.e. whether the RNA was in a form degradable into 5'-ribonucleotides by e.g. 5'-Fdase) and some of these samples were also treated with deaminase to convert the 5'-AMP into 5'-IMP. The amount of 5'-GMP, 5'-AMP and 5'-IMP in the samples (expressed as weight percentage of the disodium heptahydrate thereof based on sodium chloride free dry matter) were subsequently determined by means of HPLC according to the following method. 5'-GMP, 5'-AMP and 5'-IMP in yeast extracts were quantified by HPLC using a Whatman Partisil 10-SAX column, a phosphate buffer pH 3.35 as eluent and UV detection. Concentrations were calculated on basis of 5'-GMP, 5'-IMP and 5'-AMP standards. Sodium chloride was determined by measuring the chloride ions in the sample with a Jenway chloride meter PCLM 3 (Jenway, Essex, England) and calculating the corresponding amount of sodium chloride.

Data on RNA and 5'-ribonucleotides is presented in table 1.

TABLE 1

| Fraction | Dry matter (g)[8] | RNA (%)[1] | RNA (% of original)[3] | RNA (degr.) (%)[4] | 5'-GMP (%)[2] | 5'-AMP (%)[2] | 5'-IMP (%)[2] |
|---|---|---|---|---|---|---|---|
| Cream yeast | 360 | 8.0 | 100 | — | — | — | — |
| Autolysate[5] | 360 | 7.6 | 95 | 72 | 2.12 | 2.33 | 0 |
| Supernatant[6] | 241 | 6.6 | 55 | — | 3.22 | 3.71 | 0 |
| Cell-wall fraction | 119 | 9.7 | 40 | — | 2.71 | 2.65 | 0 |
| 2nd Supernatant[7] | 25.3 | — | — | — | 12.75 | 0 | 12.46 |

"—" Not measured
[1]Measured as weight percentage on sodium chloride free dry matter
[2]Measured as weight percentage on sodium chloride free dry matter, weight expressed as 2Na•7H$_2$O (as disodium heptahydrate salt)
[3]% RNA in the sample in respect of RNA content in the cream yeast
[4]% RNA in the sample which is in a form degradable into 5'-ribonucleotides by 5'-Fdase
[5]After heating at 65° C.
[6]After first centrifugation
[7]After Fdase & deaminase treatment and second centrifugation
[8]The dry matter comprises less than 1% w/w sodium chloride The composition containing 5'-ribonucleotides obtained with the process of the invention in this example comprises approximately 50% w/w of 5'-ribonucleotides.

The results obtained in the above described example lead to the following conclusions:
  The results show clearly that nearly all RNA present in the cream yeast remained, during the autolysis process, in a form degradable by 5'-Fdase into 5'-ribonucleotides.
  A substantial part of the RNA remained associated with the cell wall fraction of the autolysed yeast.
  An enriched RNA fraction was obtained by removal of the soluble fraction.
  The main part of the RNA in the enriched fraction was hydrolysed into 5'-ribonucleotides. These 5'-ribonucleotides were easily separated from the insoluble cell wall fraction by centrifugation or any other suitable solid/liquid separation.
  This process allows production of compositions, which are relatively high in 5'-ribonucleotides, in particular in 5'-GMP and 5'-IMP, when compared to some conventional 5'-ribonucleotide containing yeast extracts like for instance the yeast extract Maxarome Plus® (6% 5'-GMP+5'-IMP, 12% 5'-ribonucleotides) (DSM N.V., The Netherlands).
  A remarkable property of this kind of compositions containing 5'-ribonucleotides is the fact that the amount of 5'-GMP in the composition is higher than the sum of the amounts of 5'-AMP and 5'-IMP in the compositions. This is different from normal 5'-ribonucleotide containing yeast extracts, which also contain an amount of 5'-AMP derived from ATP, which can also be converted into 5'-IMP.

It will be clear to those skilled in the art that conditions as applied in this example at small scale can be applied at larger scale, optionally with some adjustments that are well within the skills and knowledge of those skilled in the art.

EXAMPLE 2

Demonstration of the Contribution of Native Yeast Enzymes During the Autolytic Process A 2 liter portion of cream yeast from *Saccharomyces cerevisiae* was heat treated for 10 minutes at 95° C. to inactivate all native yeast enzymes (control portion) and a second portion was used as such in the following extraction process.

Both portions of 2 l of cream yeast from *Saccharomyces cerevisiae* were rapidly heated to 60° C. 0.4 ml Pescalase (commercially available serine protease from DSM N.V. The Netherlands) was added to each portion and the mixtures were incubated for 4 hours at pH 6.0 and 60° C. The conditions were adjusted to pH 5.1 and 51.5° C. and an additional 2 ml of Pescalase was added to each reaction mixture. The mixtures were incubated for 20 hours at pH 5.1, 51.5° C. Finally, both portions were heated for 1 hour at 65° C. to inactivate all enzyme activity. The extracts (soluble fraction) of both incubations were separated from the insoluble cell walls by means of centrifugation.

The resulting extracts were analysed to determine the solubilisation yield and the degree of hydrolysis of the protein fraction. The solubilisation yield is herewith defined as the ratio between the amount of extract dry matter and the amount of starting material dry matter.

The results are listed in table 2.

TABLE 2

| Experiment | Enzyme inactivation | Solubilisation yield (%) | TN* (%) | AN** (%) | AN/TN Ratio | Free AA (%) |
|---|---|---|---|---|---|---|
| Control | Yes | 45 | 11.1 | 4.5 | 0.41 | 22 |
| 1 | No | 67 | 12.2 | 5.2 | 0.43 | 41 |

*TN = total nitrogen as determined according to Kjehldahl
**AN = amino nitrogen as determined according to TNBS method
AN/TN is proportional to the degree of protein hydrolysis
Free AA = free amino acids The % of free amino acid is herewith defined as the % of free amino acid in respect to the total amount of amino acid present, i.e. the sum of the free amino acids and of the amino acids bound into proteins and peptides. This percentage can be determined via HPLC by the TNBS (2,4,6-trinitrobenzenesulfonic acid) method which is known to those skilled in the art.

The results show that by applying autolysis conditions as used in experiment 1 and example 1, native yeast enzymes contribute in solubilising the cell content. In particular the native yeast enzymes are active in hydrolysing the yeast protein fraction into peptides and free amino acids.

EXAMPLE 3

Effect of Autolysis Conditions on the Conversion of RNA into 5'-Ribonucleotides and on the Partition of the RNA Between the Soluble Fraction and the Cell Wall Fraction A first 200 ml portion of cream yeast from *Saccharomyces cerevisiae* (experiment 1) was incubated for four hours at pH 6.0 and 60.0° C. in the presence of 40 µl Pescalase (commercially available serine protease from DSM Food Specialties). A second portion of 200 ml cream yeast from *Saccharomyces cerevisiae* (experiment 2) was incubated for four hours at pH 5.1 and 51.5° C. in the presence of 40 µl Pescalase. Next, the conditions of both incubation mixtures were adjusted to pH 5.1 and 51.5° C. and an additional 0.2 ml of Pescalase was added to the reaction mixtures. The mixtures were incubated for 20 hours at pH 5.1, 51.5° C. Subsequently, the enzymes were inactivated by heating the autolysates for 1 hour at 65° C. The RNA content in the autolysates and in the starting cream yeast was measured by means of HPLC as described in example 1.

Half of each reaction mixture was further incubated with the enzyme 5'-Fdase in order to determine if the RNA in the autolysates was in a form degradable into 5'-ribonucleotides. The 5'-GMP content was analysed as described in example 1.

The other half of the reaction mixture was centrifuged to determine the amount of RNA associated with the cell wall fraction.

The cell wall fractions obtained from centrifugation were incubated with 5'-Fdase to hydrolyse the RNA into 5'-ribonucleotides. The soluble fraction comprising 5'-ribonucleotides was separated from the cell wall insoluble fraction by means of centrifugation. The supernatants were analysed for 5'-ribonucleotide content and for glutamate content. The amount of glutamic acid was determined by the L-Glutamic acid Colorimetric-method for the determination of L-glutamic acid in foodstuffs and other materials test kit (Boehringer Mannheim/R-Biopharm, Enzymatic BioAnalysis/Food Analysis, Catalogue No. 10139092035, Catalogue year 2004, R-BIOPHARM AG, Darmstad, Germany). The amount of glutamate can also be measured with methods known in the art, for example by HPLC analysis.

The results of analysis are presented in table 3.

The RNA level in the starting material is 7.7% w/w on sodium chloride free dry matter. This amount of RNA can maximally lead to 2.8% w/w 5'-GMP (measured as disodium heptahydrate salt) in the autolysate after 5'-Fdase treatment (100% conversion). That means that the % of RNA degradable in 5'-ribonucleotides in experiment 1 is 78% while in experiment 2 is 21%.

The results obtained in the above-described experiments lead to the following conclusions:

RNA analysis suggests a high degree of RNA survival during autolysis in experiment 2. However, the main part of this RNA could not be degraded into 5'-ribonucleotides.

In experiment 1 the RNA in a form degradable into 5'-ribonucleotides is almost 80%.

In experiment 1 46% of RNA originally present in the microorganism remains associated with the cell wall fraction. In experiment 2, this percentage was only 12%.

The ratio glutamic acid/5'-ribonucleotides in experiment 1 is approximately 0.02.

TABLE 3

| Fraction | Exp. | Dry matter (g)[8] | RNA (%)[1] | RNA (% of original)[2] | RNA (degr.) (%)[3] | 5'-GMP (%)[4] | Glu (%)[5] |
|---|---|---|---|---|---|---|---|
| Cream yeast | 1 | 34.4 | 7.7 | 100 | — | — | — |
| Autolysate[6] | 1 | 35.0 | 7.5 | — | 78 | 2.2 | — |
| Cell-wall fraction | 1 | 8.75 | 13.9 | 46 | — | — | — |
| Supernatant[7] | 1 | 1.04 | — | — | — | 14.5 | 1.3 |
| Cream yeast | 2 | 34.4 | 7.7 | 100 | — | — | — |
| Autolysate[6] | 2 | 34.8 | 7.1 | — | 21 | 0.6 | — |
| Cell-wall fraction | 2 | 10.44 | 3.1 | 12 | — | — | — |
| Supernatant[7] | 2 | 2.50 | — | — | — | 0.8 | 1.6 |

[1]Measured as weight percentage on sodium chloride free dry matter
[2]% RNA in the sample in respect of RNA content in the cream yeast
[3]% RNA in the sample which is in a form degradable into 5'-ribonucleotides by 5'-Fdase
[4]Measured as weight percentage on sodium chloride free dry matter, weight expressed as 2Na•7H$_2$O (as disodium heptahydrate salt)
[5]Glutamic acid, measured as weight percentage on sodium chloride free dry matter
[6]After heating at 65° C.
[7]After Fdase & deaminase treatment of the cell wall fraction and centrifugation
[8]The dry matter comprises less than 1% w/w sodium chloride
"—" Not measured Summarizing the above, it is concluded that conditions applied in the first phase of the autolysis process are important in determining the amount of the RNA which remains in a form degradable into 5'-ribonucleotides. In addition, the conditions are also important in determining the amount of RNA which remains associated with the cell wall fraction.

EXAMPLE 4

Preparation of a Composition Comprising 5'-Ribonucleotides Using an Autolytic Process at Large Scale An autolytic yeast extract was produced at large scale by applying the conditions, described in example 1. The amount of RNA degradable into 5'-ribonucleotides, measured in the autolysate, was of 83% w/w (measured on sodium chloride free dry matter). The remaining cell wall fraction, obtained by centrifugation, was further treated with 5'-Fdase and deaminase to convert RNA into 5'-ribonucleotides and to convert the released 5'-AMP into 5'-IMP under conditions also described in example 1. The 5'-ribonucleotides were separated from the solids (cell walls) by ultrafiltration using a membrane with 100 kDa molecular weight cut-off, where the composition was recovered in the permeate. The permeate was concentrated by evaporation under vacuum.

The process data are presented in table 4.

TABLE 4

| Fraction | Amount (kg) | Dry matter (kg)[7] | RNA (%)[1] | RNA (% of original)[3] | 5'-GMP (%)[2] | 5'-AMP (%)[2] | 5'-IMP (%)[2] |
|---|---|---|---|---|---|---|---|
| Cream yeast | 102600 | 16926 | 7.5 | 100 | — | — | — |
| Cell wall fraction | 41140 | 5924 | 9.8 | 46 | — | — | — |
| Cell-wall fraction (after enz. treat.)[4] | 41140 | 5924 | 0.5 | 41[6] | 3.23 | 0.03 | 2.80 |
| 5'-ribonucleotides[5] | 6900 | 1104 | — | 32[5] | 13.35 | 0.13 | 11.57 |

"—" Not measured
[1] Measured as weight percentage on sodium chloride free dry matter
[2] Measured as weight percentage on sodium chloride free dry matter, weight expressed as 2Na•7H$_2$O (as disodium haptahydrate salt)
[3] % RNA in the sample in respect of RNA content in the cream yeast
[4] Cell-wall fraction after enzyme treatment with 5'-Fdase and deaminase
[5] 5'-ribonucleotide fraction after separation of the cell-walls via ultrafiltration and concentration
[6] RNA = calculated as ~4 times the weight percentage on sodium chloride free dry matter of free 5'-GMP. Free 5'-GMP on sodium chloride free dry matter is = (5'-GMP as disodium heptahydrate salt on sodium chloride free dry matter)/1.47
[7] The dry matter comprises less than 1% sodium chloride The results shown lead to the following conclusions:
The data presented in table 4 clearly demonstrate that large-scale production of 5'-ribonucleotides through the described route is feasible.
46% of the of RNA originally present in the microorganism remained associated with the cell wall fraction and could be separated from the soluble fraction by centrifugation.
The 5'-ribonucleotide composition obtained after treatment of the cell walls with 5'-Fdase and deaminase could be recovered from the solids (e.g. cell walls) by ultrafiltration.
A composition containing 53% w/w of 5'-ribonucleotides based on sodium chloride free dry matter was obtained
The 5'-GMP/(5'-IMP+5'-AMP) ratio in the composition was 1.14 (this ratio is mostly about 0.9 in conventional nucleotide containing yeast extracts).

EXAMPLE 5

Effect of the Use of Compositions Containing 5'-Ribonucleotides in Artificially Sweetened Coca Cola® or in Regular Fanta®

The effect of the addition to artificially sweetened Coca® (Coca Cola Light®—Coca Cola Company—Rotterdam) or to regular Fanta® (Fanta Orange®, Coca Cola Company—Rotterdam) of a composition containing 5'-ribonucleotides according to the invention was studied.

The composition contained 10.1% w/w of 5'-GMP, 8.7% w/w of 5'-IMP, (~40% w/w of 5'-ribonucleotides) and 0.96% w/w of glutamic acid on salt free dry matter. The sodium chloride content was <1% on dry matter. A dosage of 100 mg of composition per litre of beverage was used.

The taste and/or aroma of the beverages comprising the composition was analysed by a panel of experts in tasting of food (experiment 1 and 2) and compared with the taste of the beverages as such. In the case of Coca Cola Light®, the taste of the beverage comprising the composition was also compared with the taste of regular Coca Cola® (Coca Cola Company—Rotterdam).

The results are shown in Table 5 (Coca Cola Light®) and in Table 6 (Fanta®), respectively.

TABLE 5

| Experiment | Composition (mg/l) | Observations about taste/aroma |
|---|---|---|
| Coca Cola ® | 0.0 | Cola, acid, peaky, pungent |
| Coca Cola Light ® | 0.0 | Cola, less body, chemical after taste |
| Experiment 1 | 100.0 | Cola, no chemical after taste, clean, more body, full, more sweet, no yeasty notes where detected |

TABLE 6

| Experiment | Composition (mg/l) | Observations about taste/aroma |
|---|---|---|
| Fanta ® | 0.0 | Orange peel, acid, slightly pungent |
| Experiment 2 | 100.0 | Orange flesh, stronger, more intense, no yeasty notes where detected |

The results clearly show a positive effect of the compositions of the invention on the taste and/or aroma and/or mouthfeel of Coca Cola Light® or Fanta®. In Coca Cola Light® comprising the composition the aftertaste due to the presence of artificial sweeteners (aspartame, sodium cyclamate and acesulfame) in the beverage is masked. In the Fanta® comprising the composition the overall taste and in particular the fruity notes therein is improved.

In addition, no yeasty notes where introduced in the beverage as it would normally be the case when conventional yeast extracts were used. This demonstrates that the compositions according to the invention are clean in taste and it is especially suitable for beverage applications where the presence of a yeasty taste originating from the yeast extract or composition is not very desirable.

EXAMPLE 6

Effect of the Use of Compositions Containing 5'-Ribonucleotides in Processed Cheese The composition of example 5 was added to a low fat cheese spread (Slimkuipje® naturel 15+, produced by ERU—Woerden—The Netherlands, comprising 5% w/w fat, 14% w/w proteins, 4% w/w carbohydrates) in a dosage of 100 mg per 100 g of cheese spread. The taste and/or aroma of cheese spread comprising the composition (experiment 1) was analysed by a panel of experts in tasting of food and compared with the taste of the cheese spread as such (low fat) and with the taste of the corresponding full fat product (full fat) (Goudkuipje® naturel 48+, produced by ERU—Woerden—The Netherlands, comprising 21% w/w fat, 12% w/w proteins, 2% w/w carbohydrates).

The results are shown in table 7.

TABLE 7

| Experiment | Composition (mg/100 g) | Observations about taste/aroma |
| --- | --- | --- |
| Full fat product | 0.0 | Young Cheese taste, creamy, fatty |
| Low fat product (2) | 0.0 | Weak cheese taste, not creamy, not fatty |
| Experiment 1 | 100.0 | Stronger cheese aroma than (2), more creamy/fatty than (2), taste more similar to full fat product, no yeasty notes where detected |

The results clearly show an effect of the compositions of the invention on the taste and/or aroma and/or mouthfeel of processed cheese with low fat. In particular the taste and/or the aroma and/or the mouthfeel of the low fat spread cheese comprising the composition has more resemblance with the taste and/or the aroma and/or the mouthfeel of the full fat spread cheese.

In addition, no yeasty notes originating from the composition where introduced in the food.

EXAMPLE 7

Use of the 5'-Ribonucleotides Compositions of the Invention in the Preparation of a Yeast Extract The 5'-ribonucleotide composition obtained in example 4 was mixed with a conventional autolytic yeast extract (Gistex LS®, produced by DSM N.V.—The Netherlands, comprising 65% w/w protein, 40% free amino acids based on the total amino acid content, ~0% w/w 5'-ribonucleotides) to yield a yeast extract comprising 19.1% w/w of 5'-GMP+5'-IMP (~40% w/w 5'-ribonucleotides) on sodium chloride free dry matter) (YE 1). The effect on the taste of several types of food products of the addition of said yeast extract was compared with the effect of the addition of a commercial yeast extract comprising ~the same amount of 5'-ribonucleotides and 5'-GMP+5'-IMP (Aromild, Kohjin, Japan, comprising 21% w/w of 5'-GMP+5'-IMP and 42% w/w 5'-ribonucleotides both on sodium chloride free dry matter) (YE 2).

YE 1 and YE 2 where tested in the following types of food in 0.1% w/w concentration and in water in 0.05% w/w concentration:

Skimmed milk (0% fat)
a Optimel Vifit® "Framboos" (Campina, Woerden—The Netherlands) (probiotic milk drink with fruit taste; composition: protein: 3.0 g/100 ml, sugars: 4.5 g/100 ml, fat: 0.0 g/100 ml, calcium: 120 mg/100 ml, vitamin B2: 0.32 mg/100 ml, vitamin B6: 0.40 mg/100 ml, vitamin C: 12 mg/00 ml)
Slimkuipje® (spreadable cheese with low fat, see example 6)
Goudkuipje® (spreadable cheese, see example 6)
Fanta Orange® (see example 5)
The results are shown in Table 8.

TABLE 8

| Food Application | YE | Observations about taste/aroma |
| --- | --- | --- |
| Skimmed milk | 1 | Natural milk sensation, no after taste |
|  | 2 | Milk notes not characteristic anymore, after taste |
| Optimel ® | 1 | Strong fruit notes, full, no after taste |
|  | 2 | Strong fruit notes, cardboard after taste |
| Slimkuipje ® | 1 | Creamy, full, no sharp after taste |
|  | 2 | Sweet, astringent, sharp after taste |
| Goudkuipje ® | 1 | Creamy, full, no sharp after taste |
|  | 2 | Astringent, sharp after taste |
| Fanta ® | 1 | Strong fruit notes, full |
|  | 2 | Astringent |
| Water | 1 | Weak taste, clean |
|  | 2 | Blackcurrant after taste, wet dogs smell |

In conclusion, the yeast extract prepared from the composition of the invention as such (in water) has a cleaner taste and no aftertaste when compared with the commercial yeast extract comprising the same amount of 5'-ribonucleotides (Aromild®). In the food applications, YE 1 is cleaner in taste and improves the overall flavour of the food without adding an after taste when compared with YE 2 (Aromild®).

This example demonstrates that yeast extracts prepared using the compositions according to the invention are still cleaner in taste than commercial yeast extracts comprising the same amount of 5'-ribonucleotides.

The invention claimed is:

1. Process to produce a composition comprising 5'-ribonucleotides, the process comprising:
   a) subjecting a microorganism comprising RNA to autolysis under conditions at which at least 50% of the RNA remains in a form degradable into 5'-ribonucleotides and at which at least 20% of the RNA remains associated with the cell wall fraction;
   b) subjecting the autolysate to solid/liquid separation and recovering the RNA-containing cell wall fraction;
   c) converting the RNA in the recovered RNA-containing cell wall fraction into 5'-ribonucleotides.

2. Process according to claim 1, comprising:
   d) separating the fraction comprising 5'-ribonucleotides from the cell wall fraction.

3. Process according to claim 1, wherein autolysis in a) is initiated by at least one of: i) damaging the microbial cell walls; and ii) partially disrupting the microbial cell walls.

4. Process according to claim 3, wherein damaging the microbial cell walls, partially disrupting the microbial cell walls, or both is performed enzymatically.

5. Process according to claim 1, wherein in b) the RNA-containing cell wall fraction is recovered by centrifugation or filtration.

6. Process according to claim 1, wherein in b) the autolysate is subjected to ultrafiltration whereby a mixture of RNA-containing cell wall fraction and RNA derived from the microbial soluble fraction is recovered.

7. Process according to claim 6, wherein in c) the RNA in the recovered mixture of RNA-containing cell wall fraction and recovered RNA derived from the microbial soluble fraction are converted into 5'-ribonucleotides.

8. Process according to claim 1, wherein in c) the RNA is enzymatically converted into 5'-ribonucleotides by 5'phosphodiesterase or by 5'-phosphodiesterase and deaminase.

9. Process according to claim 1, wherein in a) at least 60% of the RNA remains in a form degradable into 5'-ribonucleotides.

10. Process according to claim 1, wherein in a) at least 70% of the RNA remains in a form degradable into 5'-ribonucleotides.

11. Process according to claim 1, wherein in a) at least 30% of the RNA remains associated with the cell wall fraction.

12. Process according to claim 1, wherein in a) at least 40% of the RNA remains associated with the cell wall fraction.

* * * * *